United States Patent
Osmundsen et al.

(10) Patent No.: US 12,344,576 B2
(45) Date of Patent: Jul. 1, 2025

(54) BED MATERIAL FOR THERMOLYTIC FRAGMENTATION OF SUGARS

(71) Applicant: HALDOR TOPSØE A/S, Kgs. Lyngby (DK)

(72) Inventors: Christian Mårup Osmundsen, Gentofte (DK); Esben Taarning, Frederiksberg (DK); Morten Boberg Larsen, Smørum (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 778 days.

(21) Appl. No.: 17/624,299

(22) PCT Filed: Aug. 13, 2020

(86) PCT No.: PCT/EP2020/072756
§ 371 (c)(1),
(2) Date: Dec. 31, 2021

(87) PCT Pub. No.: WO2021/032590
PCT Pub. Date: Feb. 25, 2021

(65) Prior Publication Data
US 2022/0411357 A1 Dec. 29, 2022

(30) Foreign Application Priority Data

Aug. 16, 2019 (DK) .......................... PA 2019 00972
Aug. 16, 2019 (DK) .......................... PA 2019 00973

(51) Int. Cl.
C07C 45/51 (2006.01)
B01J 6/00 (2006.01)
(Continued)

(52) U.S. Cl.
CPC ............ *C07C 45/51* (2013.01); *B01J 6/008* (2013.01); *B01J 8/003* (2013.01); *B01J 8/0055* (2013.01);
(Continued)

(58) Field of Classification Search
CPC ......... C07C 45/51; C07C 45/56; C07C 45/60; C07C 47/19
See application file for complete search history.

(56) References Cited

U.S. PATENT DOCUMENTS

| 4,608,357 A | 8/1986 | Silverman et al. |
| 5,397,582 A | 3/1995 | Underwood et al. |
| 2016/0348005 A1 | 12/2016 | Kulprathipanja et al. |
| 2019/0119187 A1 | 4/2019 | Larsen et al. |

FOREIGN PATENT DOCUMENTS

| EP | 0158517 B1 | 12/1991 |
| JP | 2019518011 A | 6/2019 |

(Continued)

OTHER PUBLICATIONS

Neumann, G. T. et al. "Novel Hierarchical Cerium-Incorporated MFI Zeolite Catalysts for the Catalytic Fast Pyrolysis of Lignocellulosic Biomass" ACS Catal. 2012, 2, 642-646 with Supporting Information S1-S12 (Year: 2012).*

(Continued)

*Primary Examiner* — Medhanit W Bahta
(74) *Attorney, Agent, or Firm* — Boone IP Law

(57) ABSTRACT

The present invention relates to a process for thermolytic fragmentation of a sugar into a composition comprising $C_1$-$C_3$ oxygenates. In particular, it relates to the use of heat carrying particles providing improved yields of $C_1$-$C_3$ oxygenates and improved fluidization characteristics making it suitable for industrial scale production of e.g. glycolaldehyde. It also regards a circulating fluidized bed system comprising the heat carrying particles.

29 Claims, 1 Drawing Sheet

(51) Int. Cl.
*B01J 8/00* (2006.01)
*B01J 8/08* (2006.01)
*B01J 8/18* (2006.01)
*B01J 8/38* (2006.01)
*C07C 45/56* (2006.01)
*C07C 45/60* (2006.01)
*C07C 47/19* (2006.01)

(52) U.S. Cl.
CPC .............. *B01J 8/0065* (2013.01); *B01J 8/08* (2013.01); *B01J 8/1818* (2013.01); *B01J 8/1836* (2013.01); *B01J 8/388* (2013.01); *C07C 45/56* (2013.01); *C07C 45/60* (2013.01); *C07C 47/19* (2013.01); *B01J 2208/00362* (2013.01); *B01J 2208/0038* (2013.01)

(56) References Cited

FOREIGN PATENT DOCUMENTS

| WO | 0240436 | A1 | 5/2002 |
|---|---|---|---|
| WO | 2012115754 | A2 | 8/2012 |
| WO | 2014131764 | A1 | 9/2014 |
| WO | 2017216311 | A1 | 12/2017 |
| WO | 2018057076 | A1 | 3/2018 |
| WO | 2018104508 | A1 | 6/2018 |
| WO | 2020016209 | A1 | 1/2020 |

OTHER PUBLICATIONS

International Search Report (PCT/ISA/210) and Written Opinion (PCT/ISA/237) mailed on Nov. 9, 2020, by the European Patent Office as the International Searching Authority for International Application No. PCT/EP2020/072756.

Written Opinion of the International Preliminary Examining Authority (PCT/IPEA/408) issued on Aug. 3, 2021, by the European Patent Office as the International Searching Authority for International Application No. PCT/EP2020/072756.

Office Action issued by the National Institute of Industrial Property (INPI) on Oct. 4, 2024 in related Argentinian Application No. 20200102314, 18 Pages.

Osmundsen, C. M., "Catalytic Conversion of Carbohydrates", Department of Physics Technical University of Denmark, 2013, Retrieved on Jan. 30, 2020, Retrieved from: https://backend.orbit.dtu.dk/ws/portalfiles/portal/54426932/Thesis+final.pdf. See pp. 42-58.

Search Report mailed on Feb. 3, 2020, by the Danish Patent Office for Application No. PA 2019 00973.

Office Action with English translation mailed on May 29, 2023, by the Japanese Patent Office for Japanese Application No. 2022-509673, 8 pages.

Güray Yildiz, "Validation of a new set-up for continuous catalytic fast pyrolysis of biomass coupled with vapour phase upgrading", Journal of Analytical and Applied Pyrolysis, Feb. 11, 2013, 9 pages.

Vinod Kumar Venkatakrishnan, "Oxygen removal from intact biomass to produce liquid fuel range hydrocarbons via fast-hydropyrolysis and vapor-phase catalytic hydrodeoxygenation", Royal Society of Chemistry, Oct. 6, 2014, 6 pages.

Masanori Shimizu, "Crystallization Behavior and Change in Surface Area of Alkoxide-Derived Mullite Precursor Powders with Different Compositions", Journal of the Ceramic Society of Japan, Feb. 24, 2016, 5 pages.

\* cited by examiner

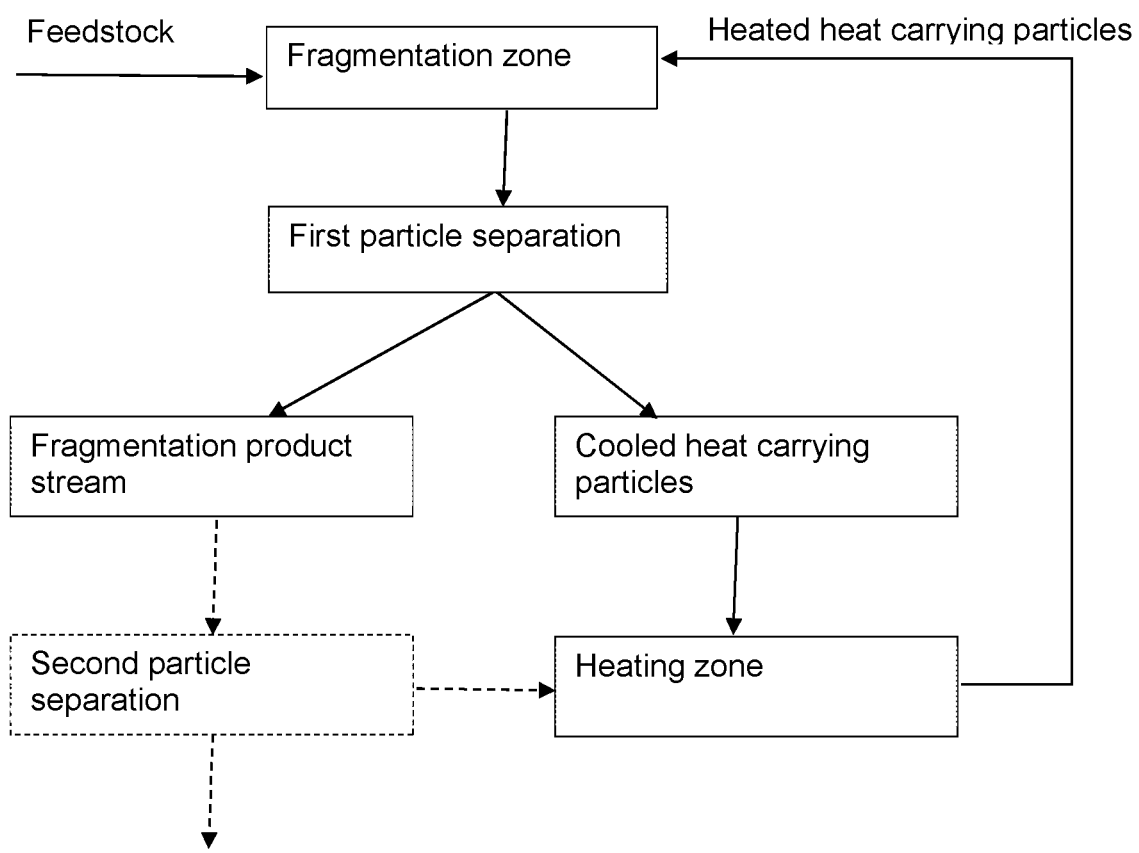

BED MATERIAL FOR THERMOLYTIC FRAGMENTATION OF SUGARS

FIELD OF THE INVENTION

The present invention relates to a process for thermolytic fragmentation of a sugar into a composition comprising $C_1$-$C_3$ oxygenates. In particular, it relates to the use of certain heat carrying particles providing improved yields of $C_1$-$C_3$ oxygenates and improved fluidization characteristics making it suitable for industrial scale production of e.g. glycolaldehyde. It also regards a circulating fluidized bed system comprising the heat carrying particles.

BACKGROUND

In recent years, increased efforts have focused on producing commercial chemicals from renewable feedstocks, such as biomass or sugars. Biomass, and sugars derived therefrom, are of particular interest due to its potential for supplementing, and possibly replacing, fossil resources as a feedstock for the preparation of commercial chemicals.

For decades, various pyrolysis processes have been under development. Pyrolysis processes refer to the thermal decomposition of carbonaceous materials at elevated temperatures in an inert atmosphere. It involves a change of chemical composition and is irreversible. The process is used for example, to produce ethylene, many forms of carbon, and other chemicals from petroleum, coal, and even wood and other biomass materials.

The conversion of biomass by pyrolysis processes is desirable due to the high volumetric production rates which can be achieved, and due to the ability of these types of processes to convert a wide range of substrates to a small range of products. However, current pyrolysis processes typically have challenges when implementing them into industrial settings, where e.g. high efficiency and long-term stability of the processes are desired for industrial applicability.

One pyrolysis method for converting carbohydrates, and in particular sugars, into commercially interesting chemicals is "thermolytic fragmentation". It may be followed by further process steps. It may also be referred to as "hydrous thermolysis" or "carbohydrate cracking". Thermolytic fragmentation is in the present context meant to refer to a selective decomposition of monosaccharides into $C_1$-$C_3$ oxygenates brought about by heating the sugar to intermediate temperatures (400-600° C.) under inert conditions and with very short residence time. The employed heating rate is very high (>1000° C./s) and the residence time low (<1 s) to minimize the selectivity to polymerization products or permanent gases.

An important chemical compound formed from thermolytic fragmentation of sugars is glycolaldehyde (hydroxyacetaldehyde). Glycolaldehyde is the smallest compound containing both a hydroxy and a carbonyl group, and it may be referred to as a sugar compound. It is a useful platform chemical for making other chemicals such as ethylene glycol and glycolic acid. It is known to be an unstable molecule at elevated temperatures. See e.g. EP 0158517 B1, which recommends low temperature vacuum distillation for purifying glycolaldehyde.

It is known that sugars can be converted by thermolytic fragmentation into a composition comprising $C_1$-$C_3$ oxygenates in a circulating fluidized bed of sand.

Such a process for thermolytic fragmentation of sugars into a $C_1$-$C_3$ oxygenate mixture in a circulating fluidized bed is described in WO 2017/216311. Sugars such as glucose are converted into $C_1$-$C_3$ oxygenate mixtures comprising glycolaldehyde. Exemplary bed materials (or heat carrying particles) are sand, silica, glass, alumina, steel, and silicon carbide. The mean particle size of the heat carrying particles is from 20-400 μm and the fragmentation takes place at a temperature in the range of from 250-900° C.

WO 2014/131764 discloses a pyrolysis process for preparing ketene from a sugar, wherein a fluidized bed material is used having a surface area of up to 600 m²/g, a pore volume of up to 0.80 ml/g, and a silanol concentration of 4.0 M. The sugar may be an aqueous solution of a sugar at a concentration of up to 60% by weight.

In WO 02/40436, an aqueous solution of sugar is converted into a glycolaldehyde rich product by hydrous thermolysis in a fluidized bed of sand (i.e. a material primarily composed of silica). An improved yield of $C_1$-$C_3$ oxygenates is achieved at a temperature around 500° C. when the thermolysis is conducted under hydrous conditions.

In U.S. Pat. No. 5,397,582 carbohydrate cracking of starch, dextrose and other sugars is described in a fluidized bed of sand. Lower yields of glycolaldehyde are obtained than in the previously mentioned prior art.

All the above disclosures present "sand" as bed material without giving many details. However, sand is not a chemical term defining a specific composition. Rather, it is a geological definition. The term "sand" generally refers to a granular material composed of finely divided rock and mineral particles. It is defined by its particle size, being finer than gravel and coarser than silt. The composition of sand varies, depending on the local rock sources and conditions, but the most common constituent of sand in inland continental settings and non-tropical coastal settings is silica (silicon dioxide, or $SiO_2$), usually in the form of quartz. The second most common type of sand is calcium carbonate, for example, aragonite. Aluminium minerals such as aluminium oxide are not common in sand and typically constitutes less than 5% of sand by weight.

The efficiency and long-term stability of prior art processes may still be improved. For instance, the bed material should be fluidizable and suitable for being circulated at a very stable and high rate for an extended period of time, and without catalyzing unwanted side-reactions.

Thus, there is still a need for improving the efficiency and long term stability and industrial applicability of bed materials for thermolytic fragmentation of sugars into a composition comprising $C_1$-$C_3$ oxygenates, including glycolaldehyde.

SUMMARY OF THE INVENTION

The present inventors, having a desire to produce high purity $C_1$-$C_3$ oxygenates on an industrial scale, have found, that using the bed materials of the prior art processes for converting a sugar into glycolaldehyde and other $C_1$-$C_3$ oxygenates by thermolytic fragmentation, still has drawbacks, even though some seem to have the necessary qualities and characteristics to provide a suitable circulating fluidized bed material. When conducting the thermolytic fragmentation process in a continuous manner, the inventors found that the yield of glycolaldehyde varied significantly with time from startup of the process. They also found that the maximum yield of $C_1$-$C_3$ oxygenates had potential for improvement. In addition, they found that some materials had fluidization problems. See e.g. examples 1A to 1E.

Glycolaldehyde is an important and valuable oxygenate product ($C_2$ oxygenate). The inventors found that to obtain a high yield of glycolaldehyde it was important not only to obtain a high selectivity towards glycolaldehyde, but also to preserve as much as possible of the glycolaldehyde formed, i.e. by reducing further conversion of the glycolaldehyde.

The inventors have now found a bed material which is suitable for use in a circulating fluidized bed and which provides improved yields of glycolaldehyde, improved fluidization characteristics and which has improved long term stability in a thermolytic fragmentation process. For industrial application it is worth noting that even a small increase in yield, selectivity and/or conversion may result in great savings.

According to an aspect of the present invention a process is provided for thermolytic fragmentation of a sugar into a composition comprising $C_1$-$C_3$ oxygenates, the process comprising:
  a. Providing a circulating, fluidized stream of heat carrying particles, wherein the heat carrying particles are circulated to a heating zone to produce heated heat carrying particles, and then the heated heat carrying particles are circulated from the heating zone to a fragmentation zone to provide heat to the fragmentation zone and producing cooled heat carrying particles, and then the cooled heat carrying particles are circulated back to the heating zone for reheating.
  b. introducing a feedstock solution comprising the sugar into the fragmentation zone of the circulating, fluidized stream of heat carrying particles to absorb heat and convert the sugar by thermolytic fragmentation into the $C_1$-$C_3$ oxygenates;
  c. separating a fragmentation product stream comprising the $C_1$-$C_3$ oxygenates from the stream of cooled heat carrying particles; and then
  d. recovering the composition comprising $C_1$-$C_3$ oxygenates from the fragmentation product stream.

In an embodiment according to the present invention, the particle surface area of the heat carrying particles is below 3 square metres per g as measured by Kr physisorption, such as below 1, 0.5, 0.2 or 0.15 square metres per g. An advantage of using heat carrying particles having a surface area as low as this is that a high yield of glycolaldehyde is obtained when converting a sugar in a thermolytic fragmentation process using such heat carrying particles. Using such heat carrying particles achieves yields of glycolaldehyde above 50% and in particular when used in a continuous process.

There is not a lower limit to the surface area of the heat carrying particles below which they will not work. However, there is a natural lower limit to the surface area of the heat carrying particles depending on preparation procedure. The lower limit is the surface area where all of the particles are perfect spheres, e.g. for particles of 70 μm it is around 0.03 m$^2$/g. Accordingly, each of the upper limits given for the surface area may have a lower limit of e.g. 0.001 or of 0.01. Thus suitable ranges could be 3-0.001 m2/g or 1-0.01 m2/g.

In another embodiment according to the present invention, at least 90% by weight of the heat carrying particles consist of silicon, aluminium and oxygen wherein the mass ratio of silicon to aluminium is from 0.25 to 1. Heat carrying particles with such composition will upon calcination at high temperatures form a large amount of mullite. Such heat carrying particles will have very low surface area (below 3 m$^2$/g) and a very low number of acid and basic sites and the fluidization characteristics are very suitable for use in a circulating fluidized bed reactor. Thus, the heat carrying particles may consist essentially of Al, Si and oxygen. It is to be understood that when the heat carrying particles are said to consist essentially of Al, Si and oxygen, the amount of oxygen bound in the structure is given by the amount of Aluminium (Al) and silicon (Si) respectively. However, some impurities may be present.

The amount of oxygen in the heat carrying particles is given by the amounts of silicon (Si) and aluminium (Al) present, since it will be bound with the stoichiometry of $SiO_2$ and $Al_2O_3$, respectively.

According to an embodiment of the present invention, the number of acid sites on the surface of the heat carrying particles is less than 3 μmol/g as measured by NH$_3$-TPD, such as less than 1, 0.5, 0.1, 0.05 or 0.01 μmol/g. Acid sites on the surface of the particles could for instance be —OH groups, such as silanol groups. According to another embodiment of the present invention, the number of basic sites on the surface of the heat carrying particles is less than 1 μmol/g as measured by CO2-TPD. An advantage of having a low amount of acid sites on the surface of the heat carrying particles is that the yield of glycolaldehyde is increased. Without being bound by theory, it is hypothesized that when the number of acid and/or basic sites is very low, then reactive reaction products, such as glycolaldehyde, pyruvaldehyde, glyoxal and acetol, are less prone to decompose into smaller molecules such as permanent gasses.

The process according to any of the embodiments of the invention is suitable for continuous operation in which case the stream of heat carrying particles is a circulating stream. Such system may be referred to as a circulating fluidized bed system, wherein the heat carrying particles are continuously recirculated between a fragmentation zone and a heating zone. An advantage of continuous operation is that that the heat carrying particles have shown to provide an increasing yield of glycolaldehyde with time on stream until a steady state yield is achieved. Steady state may be achieved after 2-4 hours on stream (TOS) but it may also take longer or shorter. It will partly depend on the reactor design and operation conditions.

It is to be understood that the amount of bed material may be adjusted whenever needed by removing or adding bed material to obtain the desired amount of bed material in the circulating fluidized bed system.

In the present context, the "recovering the composition comprising $C_1$-$C_3$ oxygenates from the fragmentation product stream" is meant to refer either to collecting the fragmentation product stream as it is without further separation or to directing the same to a subsequent step, such as to a purification unit or a hydrogenation unit.

The process according to the present invention thus provides several advantages to achieve high glycolaldehyde selectivity and a high degree of preservation of glycolaldehyde once it has been formed. The heat carrying particles used in the process according to the present invention has the advantages that they have a high melting point, a very low surface area, a low number of acidic groups per weight, a low tendency to sintering during use and during calcining, a high fluidization index and a long de-aeration time. All these characteristics, provide excellent yield of glycolaldehyde and the heat carrying particles retain their excellent fluidization characteristics for an extended period of time thus making it suitable for continuous exploitation on an industrial scale. The inventors found that materials which are generally considered to be inert particles suitable for use in fluidized beds, turned out to have some catalytic effect in the thermolytic fragmentation of sugars into $C_1$-$C_3$ oxygenates. An advantage of having a very low number of acidic and/or basic groups on the surface of the heat carrying particles is that the glycolaldehyde yield is improved.

According to another aspect of the present invention a circulating fluidized bed system is provided for fragmentation of a sugar into $C_1$-$C_3$ oxygenates, which system comprises a thermolytic fragmentation reactor comprising a fragmentation zone, a reheater comprising a heating zone, a first flow means arranged to convey fluidized bed material from the thermolytic fragmentation reactor to the reheater and second flow means arranged to convey fluidized bed material from the reheater to the thermolytic fragmentation reactor, and heat carrying particles, wherein the particle surface area of the heat carrying particles is below 3 square metres per g, such as below 1, 0.5, 0.2 or 0.15 as measured by Kr physisorption, and wherein at least 90% by weight of the heat carrying particles consist of silicium, aluminium and oxygen and the mass ratio of silicium to aluminium is from 0.25 to 1.

According to another aspect of the present invention a circulating fluidized bed system is provided for fragmentation of a sugar into $C_1$-$C_3$ oxygenates, which system comprises a thermolytic fragmentation reactor comprising a fragmentation zone, a reheater comprising a heating zone, a first flow means arranged to convey fluidized bed material from the thermolytic fragmentation reactor to the reheater and second flow means arranged to convey fluidized bed material from the reheater to the thermolytic fragmentation reactor, and heat carrying particles, wherein the number of acid sites on the surface of the heat carrying particles is less than 1 µmol/g as measured by $NH_3$-TPD, such as less than 0.5 or 0.1 µmol/g.

Such a system has the advantage of providing excellent yield of glycolaldehyde and the heat carrying particles retain their excellent fluidization characteristics for an extended period of time thus making it suitable for continuous exploitation on an industrial scale.

FIGURES

FIG. 1 is a sketch of the process according to the present invention.

DETAILED DESCRIPTION OF THE INVENTION

Definitions

In the present context the terms "bed material" "fluidized bed material" and "heat carrying particles" are used interchangeably.

It is to be understood that the stream of heat carrying particles which circulates between the to the heating zone, through the heating zone, from the heating zone to the fragmentation zone, through the fragmentation zone and from the fragmentation zone to the heating zones are the particles which make up the stream of heat carrying particles. Between the fragmentation zone and the heating zone, the stream is referred to as "cooled heat carrying particles" or "stream of cooled heat carrying particles" and between the heating zone and the fragmentation zone, the stream is referred to as "heated heat carrying particles" or "stream of heated heat carrying particles". The terms "stream of heat carrying particles", "fluidized stream of heat carrying particles", "circulating, fluidized stream of heat carrying particles" are intended to refer to the circulating stream of particles as such. The particles may be in a heated state or in a cooled stage or be in the process of giving off heat to the feedstock solution in the fragmentation zone or in the process of taking up heat in the heating zone. The stream may include the heat carrying particles and various fluids, such as carrier gas, feedstock solution comprising a sugar, $C_1$-$C_3$ oxygenates and by-products being formed from the sugar, combustion gas for heating the particles, stripping gas for removing unwanted components etc.

The term "yield" is in the present context meant to refer to the molar fraction of carbon in the carbohydrate which is converted into carbon bound in the relevant oxygenate.

The term "conversion" is in the present context meant to refer to the molar fraction of the carbohydrate which was converted into another chemical species.

The term "selectivity" is meant to refer to the molar fraction of carbon incorporated into the desired product per carbohydrate converted. The selectivity may be calculated as yield divided by conversion.

The term "calcining" or "calcined" of heat carrying particles is meant to refer to a heating of the heat carrying particles to high temperatures in a controlled atmosphere, such as air or oxygen.

Bed Materials/Heat Carrying Particles

It is to be understood that a bed material as such is composed of small particles and has the visual appearance of a powder (in the present context referred to as heat carrying particles). It comprises small solid particles, which becomes fluidized by blowing a fluidization stream through the bed material preferably in a direction against the gravitational force. When fluidized, the bed material behaves almost as a fluid. The characteristics of the particles or powder influence the fluidization behavior significantly.

Bed material powders may be grouped into four groups depending on the fluidization characteristics, which are referred to as Geldart A, B, C and D. The groups are defined by their locations on a diagram of solid-fluid density difference and particle size. The Geldart group of particles for a bed material is useful when designing fluidized beds.

The "fluidization index" is the ratio of the minimum fluidization velocity to the minimum bubbling velocity. Briefly, the minimum fluidization velocity is determined by measuring the pressure drop across a bed of solids at varying superficial gas velocities. The pressure drop will increase with increasing superficial gas velocity until a given point, where it becomes constant. The superficial gas velocity at this point is the minimum fluidization velocity. The minimum bubbling velocity is the minimum superficial gas velocity, where bubbles are observed.

For a Geldart B material the fluidization index will be one (by definition), while for a Geldart A material it will be greater than one.

The "deaeration time" is the time it takes for a fluidized bed to collapse after the fluidization gas flow is interrupted. The time can be measured by fluidizing the material at a given superficial gas velocity, which will cause the bed to expand. Interrupting the flow of gas will cause the bed to collapse; the time until a stable bed height is reached is the deaeration time. The measured time will be dependent on the procedure used, and different materials must therefore be measured with identical procedures for comparing the deaeration time.

The present inventors found during their work that the sand materials as proposed in the prior art (Example 1A) were not satisfactory as bed material in continuous, industrial scale thermolytic fragmentation processes for converting sugars into $C_1$-$C_3$ oxygenates. The inventors also found that it was not just a question of the Geldart type of the particles, which decided whether they were suitable or not.

Fluidized bed systems are used in many fields for chemical and/or thermolytic conversion of chemical compounds.

The inventors then looked in fields such as gasification of straw and support materials for Fluid Catalytic Cracking (FCC) for a suitable bed material for a continuous, industrial scale process for converting sugars into a composition comprising $C_1$-$C_3$ oxygenates (e.g. WO 2018/057076 and U.S. Pat. No. 4,608,357).

However, the inventors found (Examples 1B-1C) that these materials were not as efficient as desired for thermolytically fragmenting sugars into oxygenates in a circulating fluidized bed system. The bed material needed to be fluidisable and suitable for use in a circulating fluidized bed system and to provide high selectivity towards glycolaldehyde for an extended period of time.

The inventors realized that if the heat carrying particles were selected such that at least 90% by weight of the heat carrying particles consisted of silicium, aluminium and oxygen and the mass ratio of silicium to aluminium was from 0.25 to 1 before calcination, AND the heat carrying particles where calcined at a very high temperature, such heat carrying particles provided high yields of glycolaldehyde and good fluidization characteristics and a low tendency to sintering in a circulating fluidized bed system for thermolytic fragmentation of sugars into a composition comprising $C_1$-$C_3$ oxygenates. Such heat carrying particles were superior to any of the prior art materials.

Calcining at a very high temperature turned out to reduce the surface area even more than proposed in the prior art and resulted in bed materials which improved the yield of oxygenates and in particular of glycolaldehyde.

According to an embodiment of the invention, the heat carrying particles have been calcined at a temperature of at least 1000° C., such as in the range of from 1200 to 2000° C., from 1400-1800° C. or from 1500 to 1700° C. Surprisingly, calcining the heat carrying particles at temperatures above 1400° C., provided an ultra-low surface area which lowered the reactivity of the heat carrying particles compared to both low surface area particles and high porosity particles. In the present context an ultra-low surface area may be below 3 square metres per g as measured by Kr physisorption, such as below 1, 0.5, 0.2 or 0.15 square metres per g.

The inventors found that calcining/sintering at a high temperature such as above 1400° C., resulted in a surface having a low number of acid sites on the surface of the heat carrying particles of less than 3 μmol/g as measured by $NH_3$-TPD, such as less than 1, 0.5, 0.1, 0.05 or 0.01 μmol/g. The inventors found that having less acid sites on the surface resulted in less decomposition of the $C_1$-$C_3$ oxygenates formed during the thermolytic fragmentation and this an improved yield.

The inventors further found that when at least 90% of—or essentially all of—the heat carrying particles consisted of silicium, aluminium and oxygen and the mass ratio of silicium to aluminium was from 0.25 to 1 before calcination, a large amount of mullite was formed during calcination at high temperatures. Mullite is a rare naturally occurring silicate mineral.

Preferably, the heat carrying particles do not contain significant amounts of metals catalyzing formation of byproducts (other products than the C1-C3 oxygenates). According to an embodiment of the invention, the heat carrying particles contain less than 2%, such as less than 1% or 0.05% of catalytically active metals, such as Ti, Ni or Cu.

According to an embodiment of the present invention, the heat carrying particles has a melting point above 1100° C., such as in the range of from 1100 to 3000° C.

According to an embodiment of the invention, the fluidization index of the heat carrying particles is above 1, corresponding to a Geldart A material. According to another embodiment, 90-100%, such as 95-99.9% or 98-99.8% by weight of the heat carrying particles consist of silicium, aluminium and oxygen and the mass ratio of silicium to aluminium is of from 0.25 to 1, such as from 0.4 to 0.8 or 0.45 to 0.55.

In another embodiment at least 50% by weight, such as at least 50%, 60%, 70%, 80%, 50-99%, 60-95% or 65-90%, of the heat carrying particles consist of mullite.

Mullite in the bed material has a surprisingly advantageous effect on the fluidization properties. Such a bed material is very heat tolerant, has high strength and is very inert. In addition to mullite the heat carrying particles may comprise alpha-alumina and/or amorphous silica. Alpha-alumina provides high density particles. The presence of amorphous silica lowers the melting point of the particles. Therefore, alpha-alumina and/or amorphous silica is tolerated in the heat carrying particles, but if the amounts are too high, it has an adverse effect on the fluidization properties. Accordingly, the inventors also found that a large excess of free $SiO_2$ tended to lower the melting point of the particles and that a large excess of free $Al_2O_3$ tended to increase the density of the particles.

The heat carrying particles may have a particle density below 3.5 g/ml, such as in the range of from 2-3 g/ml, as measured by Hg porosimetry. Preferably, the Sauter mean diameter of the heat carrying particles is from 50-150 μm. The Sauter mean diameter is a general term, which is often used in fluid dynamics. It is defined as the diameter of a sphere that has the same volume/surface area ratio as a particle of interest.

The Process

In an embodiment, the fragmentation zone and the heating zone are arranged in a single reactor equipped with means for conveying the heated heat carrying particles from the heating zone to the fragmentation zone and for conveying the cooled heat carrying particles from the fragmentation zone to the heating zone.

In another embodiment, the fragmentation zone and the heating zone are arranged in separate reactors equipped with means for conveying the heated heat carrying particles from the heating zone to the fragmentation zone and for conveying the cooled heat carrying particles from the fragmentation zone to the heating zone.

According to an embodiment of the present invention the feedstock solution comprising the sugar is fed directly into the fragmentation zone of the circulating fluidized bed.

According to an embodiment of the invention, the feedstock solution comprises the sugar dissolved in a solvent. A preferred solvent is water, but also methanol, ethanol, ethylene glycol and other alcoholic or polyolic solvents may be used.

According to an embodiment of the present invention, the sugar is a mono- and/or disaccharide. Preferably, the sugar is selected from the group consisting of sucrose, lactose, xylose, arabinose, ribose, mannose, tagatose, galactose, glucose and fructose; or mixtures thereof. According to an embodiment of the invention, the concentration of sugar in the feedstock solution is between 10 and 90% by weight, such as between 20 and 90, or 30 and 90 weight %.

The composition comprising the $C_1$-$C_3$ oxygenates typically comprises one or both of the $C_2$ oxygenates glycolaldehyde and glyoxal, and/or one or both of the $C_3$ oxygenates pyruvaldehyde and acetol and/or the $C_1$ oxygenate formaldehyde. The present invention aims in particular at improving the yield of glycolaldehyde. According to an embodiment of the invention, the composition comprising $C_1$-$C_3$ oxygenates comprises one or more of glycolaldehyde, glyoxal, pyruvaldehyde, acetol and formaldehyde. However, formaldehyde is normally not preferred, since it can poison downstream catalysts and normally is not wanted in the end product. Preferably, the composition comprising $C_3$ oxygenates comprises glycolaldehyde.

When the heat carrying particles according to the present invention are employed for thermolytic fragmentation of sugars, a yield of glycolaldehyde of above 50%, such has above 60% may be obtained.

According to an embodiment of the present invention, the fragmentation zone has a fragmentation temperature in the range of from 250-900° C., such as from 300-750, 350-650, or 400-550° C. This fragmentation temperature is obtained by heating the heat carrying particles to a temperature in the range of from 300-950° C., such as from 350-800, 400-700 or 450-650° C. as measured when the heated heat carrying particles leave the heating zone. When the heat carrying particles have passed the fragmentation zone the resulting cooled heat carrying particles will have a temperature in the range of from 200-850° C., such as from 250-700, 300-600, or 350-550° C.

The fragmentation zone will normally be delimited by a reactor wall, and preferably it is delimited by a riser suitable for conducting thermolytic fragmentation of a feedstock solution comprising a sugar and suitable for fluidizing the stream of heat carrying particles. Also the heating zone will normally be delimited by a reactor wall, and preferably it is delimited by a riser suitable for heating and suitable for fluidizing the stream of heat carrying particles.

The fragmentation product stream comprising $C_1$-$C_3$ oxygenates may be separated from the stream of cooled heat carrying particles by inertial separation, such as in a cyclone. It is to be understood that when reference is made to "separating the fragmentation stream comprising $C_1$-$C_3$ oxygenates from the stream of cooled heat carrying particles" this refers to a separation of at least a fraction of the cooled heat carrying particles from the $C_1$-$C_3$ oxygenates. In an embodiment according to the present invention at least 50 weight %, such as at least 60, 70 80 or 90 weight % of the heat carrying particles are separated from the $C_1$-$C_3$ oxygenates in step c. Any remaining heat carrying particles may be removed in subsequent separation steps. The fragmentation product stream may be subjected to further process steps such as further separation steps and/or cooling steps. Accordingly, the composition comprising the $C_1$-$C_3$ oxygenates may be recovered by quench cooling of the fragmentation product stream. The fragmentation product stream or the further purified and/or cooled, such as quench cooled, fragmentation product stream may then be conveyed to further processing such as hydrogenation. According to an embodiment of the present invention, step d) of recovering the composition comprising $C_1$-$C_3$ oxygenates comprises collecting the fragmentation product stream and conveying it to a hydrogenation unit to convert the $C_1$-$C_3$ oxygenates into the corresponding poly-alcohols (e.g. glycolaldehyde and glyoxal into ethylene glycol and pyruvaldehyde and acetol into propylene glycol).

According to an embodiment of the invention, the ratio of the mass of heat carrying particles per mass of feedstock is between 12:1 and 200:1. Preferably, the feedstock is an aqueous sugar solution and the mass of feedstock is the mass of sugar dissolved in the water.

Even though the invention has been described with a focus on improving the yield of glycolaldehyde, it is to be understood that the bed material according to the present invention has the same beneficial effect on the yields of pyruvaldehyde, glyoxal and acetol.

According to an aspect of the present invention a circulating fluidized bed system is provided for fragmentation of a sugar into a composition comprising C1-C3 oxygenates, which system comprises a thermolytic fragmentation reactor comprising a fragmentation zone, a reheater comprising a heating zone, a first flow means arranged to transport (or convey) fluidized bed material from the thermolytic fragmentation reactor to the reheater and second flow means arranged to transport (or convey) fluidized bed material from the reheater to the thermolytic fragmentation reactor, and the system comprising heat carrying particles, wherein the particle surface area of the heat carrying particles is below 3 square metres per g, such as below 1, 0.5, 0.2 or 0.15 and wherein at least 90% by weight of the heat carrying particles consist of silicium, aluminium and oxygen and the mass ratio of silicium to aluminium is from 0.25 to 1.

According to an aspect of the present invention a circulating fluidized bed system is provided for fragmentation of a sugar into a composition comprising C1-C3 oxygenates, which system comprises a thermolytic fragmentation reactor comprising a fragmentation zone, a reheater comprising a heating zone, a first flow means arranged to transport (or convey) fluidized bed material from the thermolytic fragmentation reactor to the reheater and second flow means arranged to transport (or convey) fluidized bed material from the reheater to the thermolytic fragmentation reactor, and the system comprising heat carrying particles, wherein the number of acid sites on the surface of the heat carrying particles is less than 1 µmol/g as measured by NH3-TPD, such as less than 0.5 or 0.1 µmol/g. In an embodiment, the particle surface area of the heat carrying particles is below 3 square metres per g, such as below 1, 0.5, 0.2 or 0.15.

The system according to the present invention may comprise further features designed to conduct the process of the invention, such as an inlet valve for introducing the feedstock solution into the fragmentation zone, separation means for separating the fragmentation product stream from the stream of cooled heat carrying particles (such as an inertial separation unit), cooling means for cooling the fragmentation product stream (such as a condensation unit), The heating zone may be delimited by a riser or a bubbling bed reactor designed to heat the heat carrying particles according to the invention. The heating zone may accordingly comprise means for providing heat to the heating zone (such as a fuel combustion unit or a resistance heating system), The fragmentation zone may be delimited by a riser or a bubbling bed reactor designed to conduct the thermolytic fragmentation according to the invention. The means for transporting or conveying the heat carrying particles may be e.g. valves or pumps.

The invention will be further explained by the following examples.

EXAMPLES

Unless otherwise specified, the yields are given as previously defined (molar fraction of carbon bound in the carbohydrate converted per carbon bound in the relevant oxygenate produced).

Example 1A: Test of Various Silica Bed Materials

A large number of different silica (sand) materials were tested as bed material in a laboratory bubbling fluidized bed reactor. For all of the experiments, the bed material was fractioned to 90-150 μm before testing.

A bed volume (tapped volume before fluidization) of 10 mL was loaded in a bubbling fluid bed reactor (22 mm ID) and fluidized at a superficial gas velocity of approx. 50 cm/s. The temperature was increased to 500° C., at which point water was injected into the bed through a two-fluid nozzle at a rate of 0.5 g/min. Once the system reached steady state, the feed was switched to a 10 wt. % aqueous solution of glucose and time set as to. The gas leaving the reactor was cooled to 1° C. in a surface condenser, and the liquid condensate collected. The concentration of oxygenates in the condensate was determined by HPLC analysis, and the yield of oxygenates calculated based on the mass of collected product.

The mean vapor residence time in the reactor was 1-2 s. Vapor product samples were collected at steady state in the time period between 1.5 and 8.25 hours after switching the feed to aqueous glucose. The steady state yields of glycolaldehyde (GA yield) for the various bed materials can be found in Table 1.

TABLE 1

Glycolaldehyde yield for various sand bed materials

| Material | Si/Al | GA yield (carbon %) |
|---|---|---|
| Dansand #18 | 47 | 12 |
| Dansand #40 | 83 | 60 |
| Danakvarts | 177 | 54 |
| Danakvarts 018 | 60 | 2 |
| Silibeads S (Sigmund Lindner) | 81 | 60 |
| Sand (WVR) | 336 | 1 |
| Kristall-Quartzsand G11T | 470 | 42 |
| Kristall-Quartzsand G20TEAS | 793 | 60 |
| Sea sand | 155 | 1 |
| Quartz (Saint-Gobain) | 2395 | 20 |
| Sand, Fontainebleau | 2214 | 5 |

The bed materials used all had surface areas below 1 m$^2$/g. The silicium to aluminum content was in the range of from 47 to 2214. According to the Geldart classification, all of the materials are Geldart A or B and thus should fluidize well. Furthermore, the superficial gas velocity employed for the experiments was above the minimum fluidization velocity. In practice, several of the materials proved difficult to fluidize and this caused most materials to provide quite low GA yields. The results show that it was quite unpredictable from the established requirements to bed materials (or the heat carrying particles) which materials would provide high yield of GA and which would not.

Example 1B: Test of FCC Catalyst as Bed Material

A commercial FCC E-cat (available from Equilibrium Catalyst Inc) was used as bed material for the fragmentation reaction.

A bed mass of 100 g was loaded in a bubbling fluid bed reactor (42 mm ID) and fluidized at a superficial gas velocity of approx. 30 cm/s. The temperature was increased to 500° C., at which point water was injected into the bed through a two-fluid nozzle at a rate of 2 g/min. Once the system reached steady state, the feed was switched to a 10 wt. % aqueous solution of glucose and time set as to. The gas leaving the reactor was cooled to 1° C. in a surface condenser, and the liquid condensate collected. The concentration of oxygenates in the condensate was determined by HPLC analysis, and the yield of oxygenates calculated based on the mass of collected product.

TABLE 2

Characteristics of the FCC bed material

| Property | Value |
|---|---|
| Surface area [m$^2$/g] | 194 |
| D$_{3,2}$ [μm] | 70 |
| Elemental composition | Si: 22.4 wt. % |
| | Al: 22.0 wt. % |
| | La: 1.9 wt. % |
| | Ti: 1.3 wt. % |
| Phase composition (XRD) | γ-alumina: 19 wt. % |
| | Silica (amorphous): 46 wt. % |
| | Mullite: 23 wt. % |
| | FAU: 12 wt. % |

TABLE 3

Yield of glycolaldehyde for FCC catalyst as a function of time on stream

| TOS [hr] | Yield of glycolaldehyde |
|---|---|
| 2.49 | 5.2% |
| 4.49 | 8.9% |
| 6.49 | 11.9% |
| 8.49 | 14.8% |
| 10.49 | 17.1% |
| 12.49 | 19.6% |
| 14.49 | 22.2% |
| 16.49 | 25.2% |
| 18.49 | 27.3% |

Even though Mullite was present in significant amounts in the heat carrying particles and the catalyst was suitable in FCC processes, the bed material showed to be less suitable in the present invention. This may be due to a high number of acid groups on the surface of the heat carrying particles.

Example 1C: Test of Silica-Alumina With Low Surface Area as Bed Material

A spherical silica-alumina material was calcined at 1150° C., to convert it into primarily α-alumina and θ-alumina (as determined by XRD).

The material was tested using the procedure described in Example 1B.

TABLE 4

Characteristics of the FCC bed material

| Property | Value |
|---|---|
| Surface area [m$^2$/g] | 24 |
| D$_{3,2}$ [μm] | 59 |
| Elemental composition | Si: 0.7 wt. % |
| | Al: 52.1 wt. % |
| Phase composition (XRD) | α-alumina: 92 wt. % |
| | θ-alumina: 8 wt. % |

TABLE 5

Yield of glycolaldehyde for low-surface area silica-alumina bed material as a function of time on stream (TOS)

| TOS [hr] | Yield of glycolaldehyde |
|---|---|
| 3.10 | 4.7% |
| 5.10 | 8.8% |
| 7.10 | 13.4% |
| 9.10 | 18.3% |

TABLE 5-continued

Yield of glycolaldehyde for low-surface area silica-alumina bed material as a function of time on stream (TOS)

| TOS [hr] | Yield of glycolaldehyde |
|---|---|
| 11.10 | 23.2% |
| 13.10 | 27.0% |

The bed material tested in 1C, turned out to be less suitable for thermolytic fragmentation of sugar into $C_1$-$C_3$ oxygenates.

Example 1D: Test of Silica-Alumina With Low Surface Area as Bed Material

A spherical silica-alumina material was calcined at 1500° C., to convert it into primarily α-alumina and mullite (as determined by XRD).

The material was tested using the procedure described in Example 1B.

TABLE 6

Characteristics of low surface area silica-alumina bed material

| Property | Value |
|---|---|
| Surface area [m²/g] | 3 |
| $D_{3,2}$ [μm] | 51 |
| Elemental composition | Si: 0.7 wt. % |
|  | Al: 52.1 wt. % |
| Phase composition (XRD) | α-alumina: 94 wt. % |
|  | Mullite: 6 wt. % |

TABLE 7 yield of glycolaldehyde as a function of time on stream

| TOS [hr] | Yield of glycolaldehyde |
|---|---|
| 2.74 | 36.7% |
| 4.74 | 46.7% |
| 6.74 | 52.0% |
| 8.74 | 54.3% |
| 10.74 | 56.7% |
| 12.74 | 59.1% |
| 14.74 | 59.6% |
| 16.74 | 61.2% |
| 18.75 | 61.1% |

This low surface area bed material showed good yield of glycolaldehyde after a few hours on stream.

Example 1E: Test of Alumina Bed Material With Low Surface Area

A spherical alumina material was calcined at 1400 and 1600° C., respectively, which resulted in particle surface area of 1.6 m²/g and 0.1 m²/g, respectively. Both materials were completely converted to α-alumina (as determined by XRD).

The material was tested using the procedure described in Example 1B.

TABLE 8

Characteristics of the alumina bed material

| Property | Calcined at 1400° C. | Calcined at 1600° C. |
|---|---|---|
| Surface area [m²/g] | 1.6 | 0.09 |
| $D_{3,2}$ [μm] | 61 | N.D. |
| Elemental composition (measured before calcination) | Si: 34 ppm | Si: 34 ppm |
|  | Al: 53 wt. % | Al: 53 wt. % |
| Phase composition (XRD) | α-alumina: 100% | α-alumina: 100% |

TABLE 9

Yield of glycolaldehyde as a function of time on stream

| Calcined at 1400° C. | | Calcined at 1600° C. | |
|---|---|---|---|
| TOS [hr] | Yield of glycolaldehyde | TOS [hr] | Yield of glycolaldehyde |
| 2.53 | 43.5% | 2.23 | 64.3% |
| 4.53 | 52.6% | 4.23 | 69.6% |
| 6.53 | 56.3% | 6.23 | 70.5% |
| 8.53 | 58.0% | 8.23 | 68.7% |
| 10.53 | 59.9% | 10.23 | 69.7% |
| 12.53 | 60.3% | 12.23 | 69.1% |
| 14.53 | 59.5% | 14.23 | 68.3% |

Although calcination of alumina at 1600° C. led to a material which gave a high yield of glycolaldehyde, it also led to a material with a particle density of 3.8 g/ml (versus 2.6 g/ml for the material calcined at 1400° C.) which was detrimental to the fluidization properties of the material. Furthermore, significant particle sintering was observed. The material needed to be milled down to the appropriate particle size after calcination to allow for testing. This extra process step increases the cost of the materials preparation, but also importantly significantly reduced the sphericity of the material, which was detrimental for its fluidization properties.

The example shows that using heat carrying particles having a surface area of 1.6 m²/g provides a good yield of glycolaldehyde, but that using heat carrying particles having a surface area of 0.1 m²/g provides an even better yield of glycolaldehyde in thermolytic fragmentation of sugar.

Example 2: Test of New Bed Material

A silica-alumina material according to table 10, which had been calcined at 1680° C., was used as bed material for the thermolytic fragmentation reaction. The surface area of the material was 0.14 m²/g.

TABLE 10

Characteristics of the bed material according to the invention

| Property | Value |
|---|---|
| Surface area [m²/g] | 0.14 |
| $D_{3,2}$ [μm] | 88 |
| Elemental composition | Si: 16.1 wt. % |
|  | Al: 32.6 wt. % |
|  | Fe: 0.55 wt. % |
| Phase composition (XRD) | α-alumina: 4 wt. % |
|  | Mullite: 72 wt. % |
|  | Amorphous silica: 24 wt. % |

The material was tested using the procedure described in Example 1B, except for the superficial gas velocity, which was increased to 40 cm/s due to the larger particle size.

TABLE 11

Yield of glycolaldehyde as a function of time on stream

| TOS [hr] | Yield of glycolaldehyde |
|---|---|
| 1.64 | 58.7% |
| 3.64 | 68.1% |
| 5.64 | 69.3% |
| 7.64 | 68.4% |
| 9.64 | 68.2% |
| 11.64 | 68.7% |
| 13.64 | 68.9% |
| 15.65 | 68.9% |
| 17.65 | 68.9% |

For the silica-alumina material, the calcination at 1680° C. quickly leads to a high yield of glycolaldehyde, as was the case for the pure alumina material, however in this case the particle density was still only 2.9 g/ml despite the higher calcination temperature. Furthermore, no particle sintering was observed and the material was still highly spherical. Thus, the fluidization properties of the material were retained, while still obtaining a high yield of glycolaldehyde. These characteristics were retained for an extended period of time, making the heat carrying particles of this composition highly suitable for industrial application.

The invention claimed is:

1. A process for thermolytic fragmentation of a sugar into a composition comprising $C_1$-$C_3$ oxygenates, the process comprising:
   a. providing a circulating, fluidized stream of heat carrying particles, wherein the heat carrying particles are circulated to a heating zone to produce heated heat carrying particles, and then the heated heat carrying particles are circulated from the heating zone to a fragmentation zone to provide heat to the fragmentation zone and producing cooled heat carrying particles, and then the cooled heat carrying particles are circulated back to the heating zone for reheating;
   b. introducing a feedstock solution comprising the sugar into the fragmentation zone of the circulating, fluidized stream of heat carrying particles to absorb heat and convert the sugar by thermolytic fragmentation into the $C_1$-$C_3$ oxygenates;
   c. separating a fragmentation product stream comprising the $C_1$-$C_3$ oxygenates from the stream of cooled heat carrying particles; and then
   d. recovering the composition comprising $C_1$-$C_3$ oxygenates from the fragmentation product stream,
      wherein the number of acid sites on the surface of the heat carrying particles is less than 3 µmol/g as measured by $NH_3$-TPD.

2. The process according to claim 1, wherein the particle surface area of the heat carrying particles is below 3 square meters per g.

3. The process according to claim 1, wherein at least 90% by weight of the heat carrying particles consist of silicium, aluminium and oxygen and the mass ratio of silicium to aluminium is from 0.25 to 1.

4. The process according to claim 1, wherein the number of acid sites on the surface of the heat carrying particles is less than 0.5 µmol/g as measured by $NH_3$-TPD.

5. The process according to claim 1, wherein the number of basic sites on the surface of the heat carrying particles is less than 1 µmol/g as measured by $CO_2$-TPD.

6. The process according to claim 1, wherein the fluidization index of the heat carrying particles is above 1.

7. The process according to claim 1, wherein 90-100% by weight of the heat carrying particles consist of silicium, aluminium and oxygen and the mass ratio of silicium to aluminium is of from 0.25 to 1.

8. The process according to claim 1, wherein at least 50% by weight of the heat carrying particles consist of mullite.

9. The process according to claim 1, wherein the heat carrying particles have been calcined at a temperature of at least 1000° C.

10. The process according to claim 1, wherein the heat carrying particles has a melting point above 1100° C.

11. The process according to claim 1, wherein the particle density of the heat carrying particles is below 3.5 g/ml, as measured by Hg porosimetry.

12. The process according to claim 1, wherein the Sauter mean diameter of the heat carrying particles is from 50-150 µm.

13. The process according to claim 1, wherein the feedstock solution comprising the sugar is fed directly into the fragmentation zone.

14. The process according to claim 1, wherein the sugar is a mono- and/or di-saccharide.

15. The process according to claim 1, wherein the feedstock solution comprises an aqueous solution of a sugar selected from the group consisting of sucrose, lactose, xylose, arabinose, ribose, mannose, tagatose, galactose, glucose and fructose; or mixtures thereof.

16. The process according to claim 1, wherein the concentration of sugar in the feedstock solution is between 10 and 90% by weight.

17. The process according to claim 1, wherein the composition comprising the $C_1$-$C_3$ oxygenates comprises one or more of glycolaldehyde, glyoxal, pyruvaldehyde, acetol and formaldehyde.

18. The process according to claim 1, wherein the fragmentation zone has a fragmentation temperature in the range of from 250-900° C.

19. The process according to claim 1, wherein the heated heat carrying particles have a temperature in the range of from 300-950° C., as measured when the heated heat carrying particles leave the heating zone.

20. The process according to claim 1, wherein the cooled heat carrying particles have a temperature in the range of from 200-850° C., as measured when the cooled heat carrying particles leave the fragmentation zone.

21. The process according to claim 1, wherein the fragmentation zone is delimited by a riser suitable for conducting thermolytic fragmentation of a feedstock solution comprising a sugar and suitable for fluidizing the stream of heat carrying particles.

22. The process according to claim 1, wherein the heating zone is delimited by a riser suitable for heating and suitable for fluidizing the stream of heat carrying particles.

23. The process according to claim 1, wherein the fragmentation product stream is separated from the stream of cooled heat carrying particles by inertial separation.

24. The process according to claim 1, wherein the composition comprising the $C_1$-$C_3$ oxygenates is recovered by quench cooling of the fragmentation product stream.

25. The process according to claim 1, wherein the ratio of the mass flow rate of heat carrying particles per mass flow rate of feedstock is between 12:1 and 200:1.

26. The process according to claim 1, wherein step d) of recovering the composition comprising $C_1$-$C_3$ oxygenates comprises collecting the fragmentation product stream and conveying it to a hydrogenation unit to convert the $C_1$-$C_3$ oxygenates into the corresponding poly-alcohols.

27. A process for thermolytic fragmentation of a sugar into a composition comprising $C_1$-$C_3$ oxygenates, the process comprising:
  a. providing a circulating, fluidized stream of heat carrying particles, wherein the heat carrying particles are circulated to a heating zone to produce heated heat carrying particles, and then the heated heat carrying particles are circulated from the heating zone to a fragmentation zone to provide heat to the fragmentation zone and producing cooled heat carrying particles, and then the cooled heat carrying particles are circulated back to the heating zone for reheating,
  b. introducing a feedstock solution comprising the sugar into the fragmentation zone of the circulating, fluidized stream of heat carrying particles to absorb heat and convert the sugar by thermolytic fragmentation into the $C_1$-$C_3$ oxygenates;
  c. separating a fragmentation product stream comprising the $C_1$-$C_3$ oxygenates from the stream of cooled heat carrying particles; and then
  d. recovering the composition comprising $C_1$-$C_3$ oxygenates from the fragmentation product stream,
  wherein the particle surface area of the heat carrying particles is below 3 square meters per g,
  wherein at least 90% by weight of the heat carrying particles consist of silicium, aluminium and oxygen and the mass ratio of silicium to aluminium is from 0.25 to 1.

28. A process for thermolytic fragmentation of a sugar into a composition comprising $C_1$-$C_3$ oxygenates, the process comprising:
  a. providing a circulating, fluidized stream of heat carrying particles, wherein the heat carrying particles are circulated to a heating zone to produce heated heat carrying particles, and then the heated heat carrying particles are circulated from the heating zone to a fragmentation zone to provide heat to the fragmentation zone and producing cooled heat carrying particles, and then the cooled heat carrying particles are circulated back to the heating zone for reheating;
  b. introducing a feedstock solution comprising the sugar into the fragmentation zone of the circulating, fluidized stream of heat carrying particles to absorb heat and convert the sugar by thermolytic fragmentation into the $C_1$-$C_3$ oxygenates;
  c. separating a fragmentation product stream comprising the $C_1$-$C_3$ oxygenates from the stream of cooled heat carrying particles; and then
  d. recovering the composition comprising $C_1$-$C_3$ oxygenates from the fragmentation product stream,
    wherein the number of basic sites on the surface of the heat carrying particles is less than 1 µmol/g as measured by $CO_2$-TPD.

29. The process according to claim 1, wherein the number of acid sites on the surface of the heat carrying particles is less than 1 µmol/g as measured by $NH_3$-TPD.

* * * * *